US008055333B2

(12) United States Patent
Duann et al.

(10) Patent No.: US 8,055,333 B2
(45) Date of Patent: Nov. 8, 2011

(54) DEVICE AND METHOD FOR DETECTING CARDIAC IMPAIRMENTS

(76) Inventors: Jeng-Ren Duann, San Diego, CA (US); Tzyy-Ping Jung, San Diego, CA (US)

( * ) Notice: Subject to any disclaimer, the term of this patent is extended or adjusted under 35 U.S.C. 154(b) by 516 days.

(21) Appl. No.: 11/841,300

(22) Filed: Aug. 20, 2007

(65) Prior Publication Data

US 2008/0183093 A1     Jul. 31, 2008

Related U.S. Application Data

(63) Continuation-in-part of application No. 10/482,931, filed as application No. PCT/US02/21277 on Jul. 3, 2002, now Pat. No. 7,941,205.

(60) Provisional application No. 60/303,325, filed on Jul. 5, 2001.

(51) Int. Cl.
*A61B 5/0452*     (2006.01)
(52) U.S. Cl. ......... 600/516; 600/515; 600/518; 600/523
(58) Field of Classification Search .......... 600/508, 600/515, 516, 518, 523
See application file for complete search history.

(56) References Cited

U.S. PATENT DOCUMENTS

| 4,974,598 | A | * | 12/1990 | John | 600/509 |
|---|---|---|---|---|---|
| 5,042,499 | A | * | 8/1991 | Frank et al. | 600/509 |
| 5,215,099 | A | | 6/1993 | Haberl et al. | |
| 5,439,004 | A | | 8/1995 | Duong-Van et al. | |
| 5,687,737 | A | | 11/1997 | Branham et al. | |
| 5,706,402 | A | * | 1/1998 | Bell | 706/22 |
| 5,967,995 | A | * | 10/1999 | Shusterman et al. | 600/516 |
| 6,152,883 | A | | 11/2000 | Blanchett et al. | |
| 7,092,748 | B2 | * | 8/2006 | Valdes Sosa et al. | 600/407 |
| 2003/0208109 | A1 | | 11/2003 | David et al. | |
| 2004/0019287 | A1 | | 1/2004 | White | |
| 2004/0054295 | A1 | | 3/2004 | Ramseth | |
| 2004/0073127 | A1 | | 4/2004 | Istvan et al. | |
| 2004/0193064 | A1 | * | 9/2004 | Shusterman | 600/504 |

FOREIGN PATENT DOCUMENTS

| EP | 1190671 | A2 | 3/2002 |
|---|---|---|---|
| EP | 1773188 | A1 | 4/2007 |
| WO | 8706446 | A1 | 11/1987 |
| WO | 0124876 | A1 | 4/2001 |

OTHER PUBLICATIONS

Barros et al., Removing artifacts from electrocardiographic signals using independent components analysis, Neurocomputing, 1998, pp. 173-186, vol. 22, Iss. 1-3, Elsevier, London, UK.

(Continued)

*Primary Examiner* — Scott Getzow
*Assistant Examiner* — Joseph Dietrich
(74) *Attorney, Agent, or Firm* — Anatoly S. Weiser; Daniel M. Chambers; Acuity Law Group, P.C.

(57) ABSTRACT

Electrocardiogram (ECG) recorded signals are processed by a computer-implemented method to substantially remove extraneous signals to produce intermediary signals, and to separate the intermediary signals using a non-orthogonal transformation method such as independent component analysis to produce independent components of signals. The separated signals are displayed to help physicians to analyze medical conditions and to identify locations of abnormal heart conditions.

24 Claims, 10 Drawing Sheets

OTHER PUBLICATIONS

De Lathauwer et al., Fetal Electrocardiogram Extraction by Blind Source Subspace Separation, IEEE Transactions on Biomedical Engineering, 2000, pp. 567-572, vol. 47, No. 5, IEEE Service Center, Piscataway, NJ, US.

Jung et al., Independent Component Analysis of Biomedical Signals, Proc. 2nd Int'l Workshop on Independent Component Anal. and Blind Signal Separation, 2000, pp. 633-644, Helsinki, Finland.

Potter et al., Competing ICA techniques in biomedical signal analysis, Electrical and Computer Engineering, Canadian Conference on May 13-16, 2001, IEEE, 2001, pp. 987-992, vol. 2, IEEE Service Center, Piscataway, NJ, US.

Zarzoso et al., Noninvasive Fetal Electrocardiogram Extraction: Blind Separation Versus Adaptive Noise Cancellation, IEEE Transactions on Biomedical Engineering, 2001, pp. 12-18, vol. 48, No. 1, IEEE Service Center, Piscataway, NJ, US.

* cited by examiner

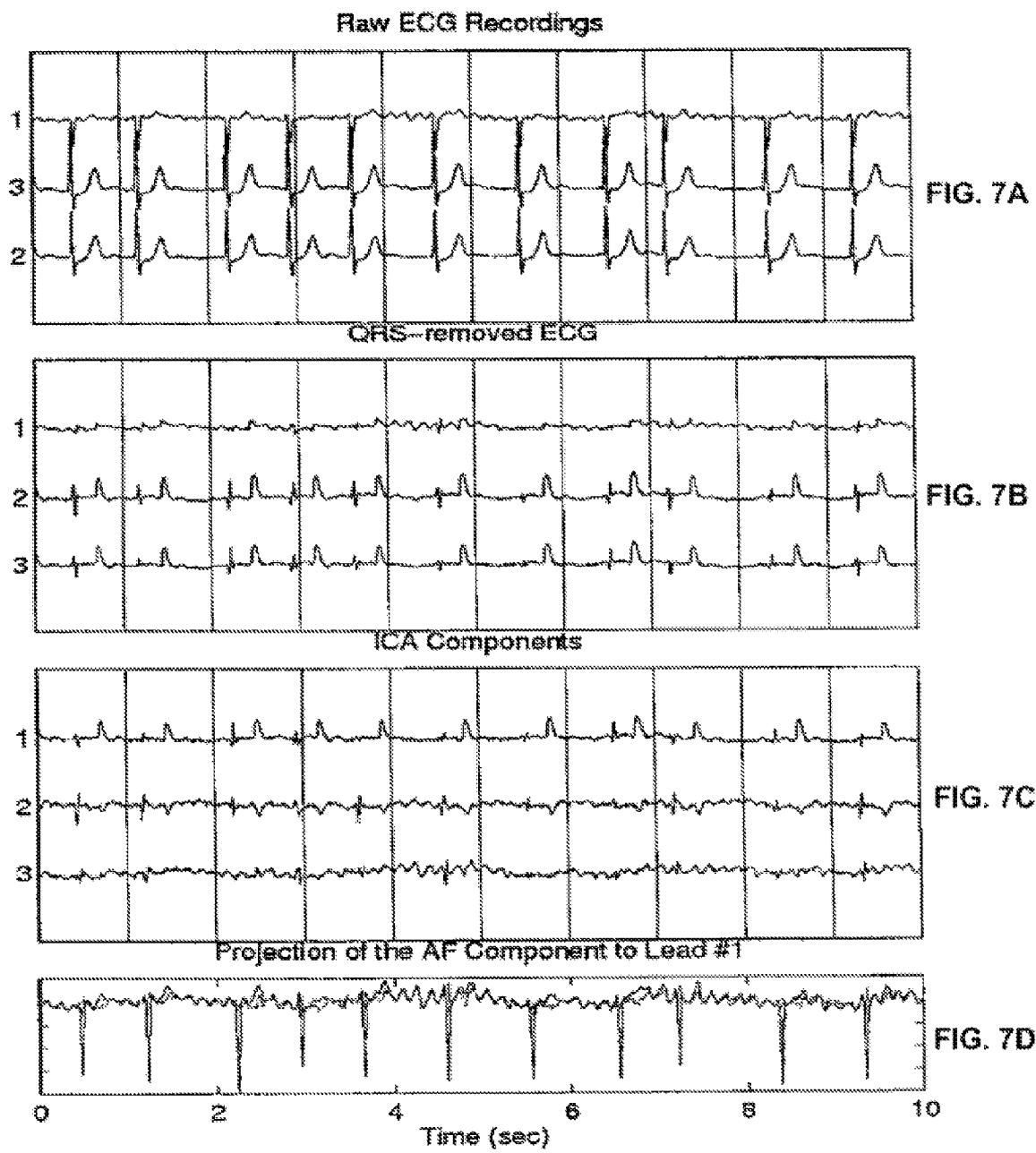

DEVICE AND METHOD FOR DETECTING CARDIAC IMPAIRMENTS

RELATED APPLICATIONS

This application is a continuation-in-part of U.S. patent application Ser. No. 10/482,931 now U.S. Pat. No. 7,941,205, entitled "System and Method for Separating Cardiac Signals"; which is a national phase filing of International patent application number PCT/US02/21277, filed Jul. 3, 2002, and entitled "System and Method for Separating Cardiac Signals"; which claimed priority to U.S. patent application No. 60/303,325, filed Jul. 5, 2001; all of which are incorporated herein in their entirety.

BACKGROUND OF THE INVENTION

1. Field of the Invention

The present invention relates to the field of medical devices and methods for processing cardiac signals.

2. Description of the Related Art

Electrocardiogram (ECG or EKG) recording is a valuable tool for physicians to study patient heart conditions. In a typical 12-lead arrangement, up to 12 sensors are placed on a subject's chest or abdomen and limbs to record the electric signals from the beating heart. Each sensor, along with a reference electrode, forms a separate channel that produces an individual signal. The signals from the different sensors are recorded on an ECG machine as different channels. The sensors are usually unipolar or bipolar electrodes or other devices suitable for measuring the electrical potential on the surface of a human body. Since different parts of the heart, such as the atria and ventricles, produce different spatial and temporal patterns of electrical activity on the body surface, the signals recorded on the ECG machine are useful for analyzing how well individual parts of the heart are functioning.

A typical heartbeat signal has several well-characterized components. The first component is a small hump in the beginning of a heartbeat called the "P-Wave". This signal is produced by the right and left atria. There is a flat area after the P-Wave which is part of what is called the PR interval. During the PR interval the electrical signal is traveling through the atrio-ventricular node (AV) node. The next large spike in the heartbeat signal is called the "QRS Complex." The QRS Complex is a tall, spiked signal produced by the ventricles. Following the QRS complex is another smaller bump in the signal called the "T-Wave," which represents the electrical resetting of the ventricles in preparation for the next signal. When the heart beats continuously, the P-QRS-T waves repeat over and over.

The measurements can be used to determine such features as the underlying rate and rhythm mechanism of the heart, the orientation of the heart (how it is placed) in the chest cavity, evidence of increased thickness (hypertrophy) of the heart muscle, evidence of damage to the various parts of the heart muscle (myocardium), evidence of acutely impaired blood flow to the heart muscle, or patterns of abnormal electric activity that may predispose the patient to abnormal cardiac rhythm disturbances. More specifically, such information can identify abnormally fast (tachycardia) slow (bradycardia) or irregular heart rhythms (arrhythmias), abnormal conduction of cardiac impulses—which may suggest underlying cardiac or metabolic disorders, occurrence of a prior heart attack (myocardial infarction), an evolving and/or acute heart attack, an acute impairment to blood flow to the heart during an episode of a threatened heart attack (unstable angina or coronary artery disease), adverse effects on the heart from various heart diseases or systemic diseases (such as high blood pressure, thyroid conditions, heart valve diseases, dilated cardiomyopathy, or other myocardial defects, etc.), adverse effects on the heart from certain lung conditions (such as emphysema, pulmonary embolus (blood clots to lung), etc.), certain congenital heart abnormalities, abnormal blood electrolytes (e.g., potassium, calcium, magnesium), inflammation of the heart or its lining (myocarditis, pericarditis).

The rhythm analysis first determines the origins of the predominant rhythm in the sample and chooses from the major categories consisting of electronic atrial pacing, atrial flutter, ectopic atrial rhythm, sinus rhythm, junction rhythm and atrial fibrillation, including asystole, tachycardia, trigeminy, bradycardia, bigeminy and atrial and ventricular fibrillations, pacemakers, implantable cardioverter defibrillator, electrical alternans—pericardial effusion, and the like. The morphology interpretation will determine the existence of ischaemic heart diseases and syndromes such as Wolff-Parkinson-White, Long QT interval Romano-Ward Syndrome and Lown-Ganong-Levine Syndrome, hypertrophy patterns such as stenosis, QRS abnormalities such as low voltage QRS, pulmonary disease pattern, QRS axis, conduction abnormalities, ventricular hypertrophy, infarction, ST+T abnormality with ventricular hypertrophy, dating infarcts, epicardial injury, pericarditis, early repolarization, nonspecific ST elevation, subendocardial injury, nonspecific ST depression, digitalis effect, junctional ST depression, ischemia, QRS-T angle and QT interval, atrioventricular (AV) block, acute pulmonary embolus, bundle branch block, hyper- and hypo-kalaemia, piggy-back heart transplant, digitalis effect, ST deviation, and other normal and abnormal signals.

Many publications have described studying cardiac signals and detecting abnormal heart conditions. Sample publications include U.S. Patent Publication No. 20020052557; Podrid & Kowey, Cardiac Arrhythmia: Mechanisms, Diagnosis, and Management Lippincott Williams & Wilkins Publishers (2nd edition, Aug. 15, 2001); Marriott & Conover, Advanced Concepts in Arrhythmias, Mosby Inc. (3rd edition, Jan. 15, 1998); and Josephson, M. E., Clinical Cardiac Electrophysiology: Techniques and Interpretations, Lippincott Williams & Wilkins Publishers; ISBN (3rd edition, Dec. 15, 2001).

Unfortunately, although ECG signals have been studied for decades, they are difficult to assess because ECG signals recorded at the surface of the skin or at the surface of the heart are mixtures of signals from multiple sources. Typically, it is relatively straightforward to measure the shape of the QRS complex since this signal is so strong. However, irregular shaped P-wave or T-wave signals, along with weak irregular oscillatory signals that suggest a heart arrhythmia are often masked by large pacemaker signals, or the strong QRS complex signals. Thus, it can be very difficult to isolate small irregular oscillatory signals and to identify arrhythmia conditions.

In addition, atrial and ventricular signals are sometimes undesirably superimposed over one another. In many cases, diagnosis of disease states requires these signals to be separated from one another. For example, it might be desirable to separate P wave signals from QRS complex signals, so that signals originating in an atrium are isolated from signals representing concurrent activities in the ventricle.

In some practices the ECG signals are electronically "filtered" by excluding signals of certain frequencies. Typically, filters are applied to ECG signals to remove extraneous signals or disturbances, such as those due to baseline drift, power line interference and interferences from other physiological sources. The signals may also be "averaged" to remove largely random or asynchronous data, which is assumed to the meaningless "noise." The filtering and averaging methods irreversibly eliminate portions of the recorded signals, including information that may be important to an accurate diagnosis. In addition, it is not known whether the more random data is truly "noise" and thus meaningless to an evaluation of the heart's condition. It might be that the signals removed by filtering are indicative of a disease state in a patient. One filtering method is disclosed in U.S. Pat. No. 6,308,094 entitled "System for prediction of cardiac arrhythmias," which uses Karhunen Loeve Transformation to reduce or compress cardiac signals into elements that are deemed "significant." As a result, the information that is deemed "insignificant" is lost.

Compared to other signal separation applications, separating ECG recording signals presents additional challenges. For example, the sources are not always stationary since the heart chambers contract and expand during beating. Additionally, the activity of a single chamber may be mistaken for multiple sources because of the presence of moving waves of electrical activity across the heart. If electrodes are not securely attached to the patient, or if the patient moves (for example older patients may suffer from uncontrolled jittering), the movement of the electrodes also undesirably generates signals. In addition, multiple signals can be sensed by the ECG which are unrelated to the cardiac signature, such as myopotentials, i.e., electrical signals from muscles other than the heart.

In addition, typically up to 12 leads of sensors are placed on the chest, torso, limbs, abdomen and/or back of a patient to enable the recording of multiple signals. Since each sensor generates one channel of an electronic signal, multiple sensors accommodate the recording of multiple signals. The signals are processed in the electrocardiogram device, and a display or recording is generated for use by medical personnel. The medical personnel, using their skills and training, evaluate the results to find and diagnose an abnormal cardiac signal. By using multiple channels of signals, the electrocardiogram can be used to identify or isolate abnormal heartbeats for evaluation and diagnostic purposes. However, it is time consuming and cumbersome to place multiple sensors and route their associated leads to the electrocardiogram. Further, such multi-lead packs are costly, may not be appropriately used in temporary or emergency situations, and impractical for medical personnel unless read through a long-term ECG recording for labeling abnormal heartbeats. When a 12-lead system can not be used, fewer leads may be applied, but there may be an associated decrease in the quality and detail in the resulting electrocardiogram recording. For example, a 3-lead sensor such as a Holter system may be used, typically to record the cardiac condition of a patient who is away from a hospital bed or stays at home.

Unfortunately, each channel (lead) of recorded ECG signals is typically a combination of signals from multiple sources originating from events occurring at different compartments of the heart, and strong signals such as QRS complex signals typically dominate other signals. Unwanted signals from other sources, such as signals generated by pacemakers or by non-cardiac muscle movements (such as the trembling of an elderly patient), may be included and combined in the ECG recordings. Therefore, it is desirable to separate the ECG signals into components of independent sources so that the separated components can be used for medical analysis of the patient's condition. For example, copending U.S. patent application Ser. No. 10/482,931, entitled "System and Method for Separating Cardiac Signals", discloses a system for separating a cardiac signal into its independent sources by using an independent component analysis process, and is incorporated herein by reference. Once separated, the components may be displayed or otherwise used for diagnosis and treatment.

Devices with 1 or more sensors are used in various scenarios, such as automated external defibrillators or other situations when the more robust 12-lead sensors can not be used. Compared to 12-lead, devices with less sensors are more affordable, easier to store, and easier to use. However, fewer sensors typically provide less detailed cardiac information, and are therefore useful for general evaluation only. Since only limited information may be derived from fewer lead systems, an incorrect or incomplete evaluation and diagnosis may be made, which may result in long-term medical complications or even death. Accordingly, the fewer lead system is typically replaced with a multiple-lead system (preferably a 12-lead system) as soon as practical.

SUMMARY OF THE INVENTION

Briefly, the present invention provides a process and system to decompose a cardiac signal, such as an electrocardiogram (ECG) signal, into components. The components are then usable to assist in the detection and location of an abnormal heart condition or anomaly, such as arrhythmias of a heart. More specifically, the present application exploits the information extracted from prior training or knowledge to filter, isolate or suppress "extraneous" features or sources in the ECG signal prior to introducing the processed ECG signal to a signal separation process. For example, the fewer independent signals that are introduced, or the more prominently important sources can be presented, the more efficient and likely the signal separation process will be in extracting the desirable signal, and in this case, supporting the diagnosis of cardiac disease and abnormalities.

The cardiac signal is preprocessed to remove extraneous features and then presented as inputs to a signal separation process, which separates the cardiac signal into a set of components. The components may be grouped according to predefined criteria. The components or groups may be analyzed or displayed to assist in the detection of an abnormal cardiac signal, which may be indicative of an abnormal heart condition. In one example, the signal separation process is a non-orthogonal transformation method such as independent component analysis (ICA).

For example, the disclosed systems and methods can be applied to suggest the location of atrial fibrillation, and to locate arrhythmogenic regions of a chamber of the heart using heart cycle signals measured from a body surface of the patient. Non-invasive localization of the ectopic origin allows focal treatment to be quickly targeted to effectively inhibit these complex arrhythmias without having to rely on widespread and time consuming sequential searches or on massively invasive simultaneous intracardiac sensor technique. The effective localization of these complex arrhythmias can be significantly enhanced by providing preprocessed source data to the independent component analysis. The signal separation process is thereby enabled to separate initially superimposed heart cycle signals originating from differing chambers or regions of the heart tissue.

By reviewing or comparing established health patterns and established abnormal patterns with the patterns of the patient, a user is able to assess the likelihood of abnormality in the signals, which indicate disease conditions in the patient. Cardiac abnormalities, whether congenital or acquired, include arrhythmia, bradycardia, tachycardia, fibrillation, infarction, ischemial, long-QT syndrome, blocks, late potentials and premature contractions.

Still another aspect of the invention relates to a medical system for separating cardiac signals. The system includes a signal receiving module to receive recorded cardiac signals from medical sensors; a process for removing extraneous signals such as a QRS complex removal module to substantially remove QRS complex signals from the received cardiac signals to generate a preprocessed signal; a separation module using independent component analysis to separate the cardiac signals into independent sources using the preprocessed input signal; and a display module to display the separated signals. In some embodiments, the number of medical sensors is less than 12, for example, 2, 3, 4, 5, 6, 7, 8, 9, or 11 leads, or greater than 12.

Other aspects and embodiments of the invention are described below in the detailed description section or defined by the claims.

BRIEF DESCRIPTION OF THE DRAWINGS

FIG. 7A illustrates a series of recorded 3-lead ECG signals. FIG. 7B illustrates the series of recorded 3-lead ECG signals with QRS complex signals substantially removed. FIG. 7C illustrates the series of recorded 3-lead ECG signals with QRS complex signals substantially removed and separated by an independent component analysis method. FIG. 7D illustrates a component of the separated ECG signals projected to a lead of the recorded signals.

DETAILED DESCRIPTION OF THE PREFERRED EMBODIMENT

Embodiments of the invention relate to a system and method for accurately separating medical signals in order to determine disease states in a patient. In one embodiment, the system analyzes ECG signals in order to determine whether a patient has a heart ailment or irregularity. As discussed in detail below, embodiments of the system utilize the techniques of independent component analysis to separate the medical signals from one another.

In addition to the signal separation technique, embodiments of the invention also relate to systems and methods that first identify, attenuate, remove, isolate or suppress extraneous signals. Such extraneous signals can be signals derived from baseline drift, power line or other electrical and magnetic interference, motion artifacts, instrumentation noise generated by external sources, electrode contact noise, or interferences from other physiological sources, for example. Other physiological sources can include breathing, movement, or other signals generated from non-myocardial sources. Alternatively, depending on the desirable signal, the extraneous signal can be a signal of myocardial origin, such as when separating atrial and ventricular signals. One such signal that can be suppressed is the QRS complex, which in some cases is so strong or dominant that it can mask important signal sources. The QRS is typically derived from identifying the R wave.

Figure 1:
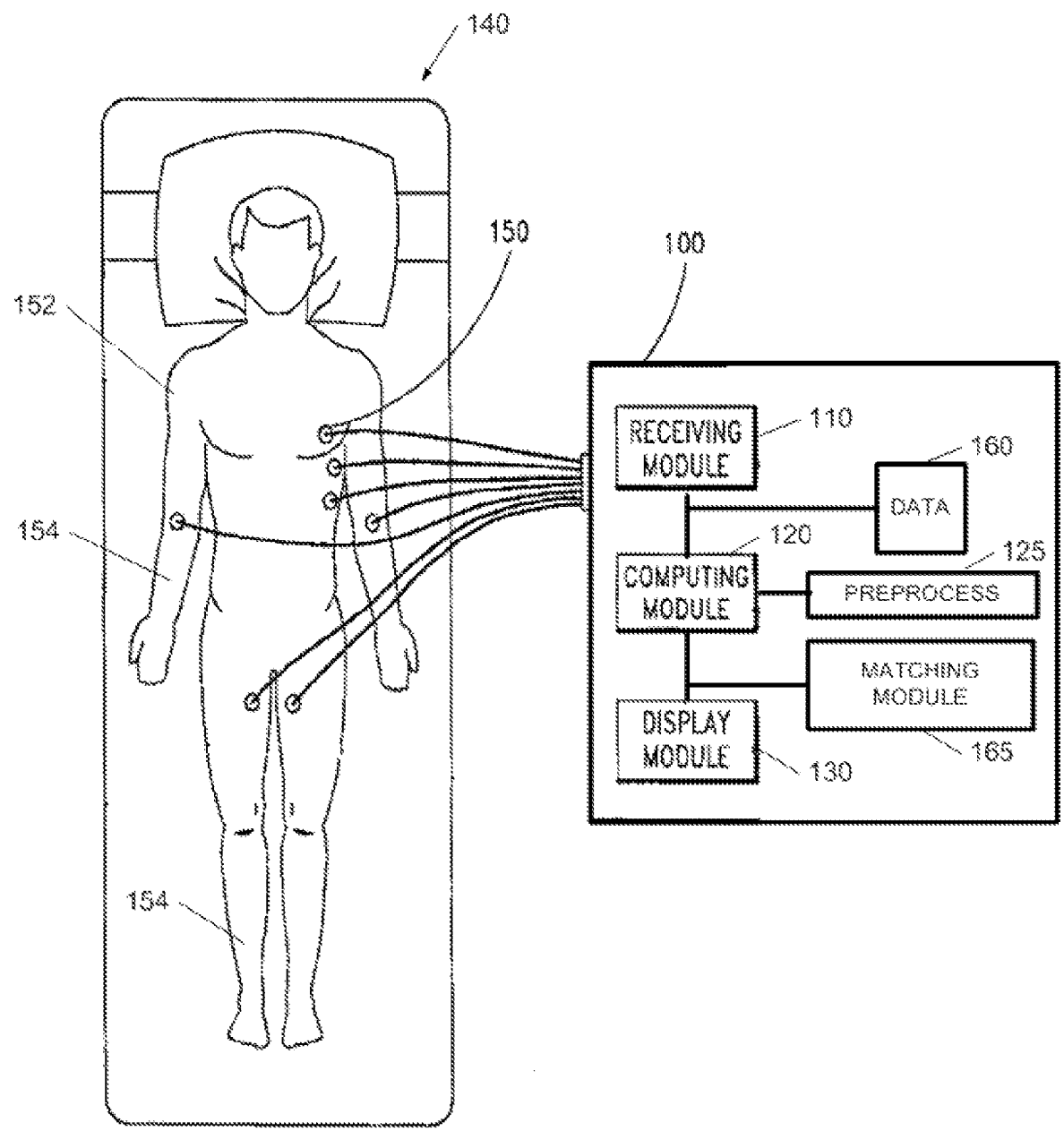
FIG. 1 is a diagram of an ECG system according to one embodiment of the invention.

FIG. 1 is a diagram of an ECG system 100 that includes a computing module 120 for signal separation according to one embodiment of the present invention. As shown in FIG. 1, electrode sensors 150 are placed on the chest 152 and limbs 154 of a patient 140 to record electric signals. The electrode sensors 150 send the electric signals to a receiving module 110 of the ECG system 100. After optionally performing signal amplification, analog-to-digital conversion or both, the receiving module 110 sends the received signals to the computing module 120 of the ECG system 100. The computing module 120 uses an independent component analysis method to separate the recorded signals to produce separated signals. In some cases, the computing module 120 may also cooperate with a preprocess module 125, which may be used to identify, attenuate, remove, or suppress unwanted on extraneous signals. The preprocessor 125 may be part of the computing module, or may be provided as a discrete component or module. Further, the preprocessor may be algorithmic in nature, may use analog or other hardware devices, or may be implemented as a combination of hardware, software, or firmware.

The computing module 120 can be implemented in hardware, software, or a combination of both. It can be located physically within the ECG system 100 or connected to the recorded signals received by the ECG system 100. A displaying module 130, which includes a printer or a monitor, displays the separated signals on paper or on screen. The displaying module 130 can be located within the ECG system 100 or connected to it. Optionally, the displaying module 130 may display the recorded signals on paper or on screen. In one embodiment, the displaying module 130 also displays some components of the separated signals in a chaos phase space portrait.

In one embodiment, the ECG system 100 also includes a database 160 that stores recognized ECG signal triggers and corresponding diagnosis. The triggers refer to conditions that indicate the likelihood of arrhythmia in a patient. For example, triggers can include abnormal sinus rhythm, premature sinus beats, beats following long sinus pauses, long-short beat sequences, R on T-wave beats, ectopic ventricular beats, premature ventricular beats, and so forth. Triggers can include threshold values that indicate arrhythmia, such as threshold values of ST elevations, heart rate, increase or decrease in heart rate, late-potentials, abnormal autonomic activity, and so forth. A left bundle-branch block diagnosis can be associated with triggers such as the absence of q wave in leads I and V6, a QRS duration of more than 120 msec, small notching of R wave, etc.

Triggers can be based on a patient's history, for example the percentage of abnormal beats detected during an observation period, the percentage of premature or ectopic beats detected during an observation period, heart rate variation during an observation period, and so forth. Triggers stored in the database 160 may also include, for example, the increase or decrease of ST elevation in beat rate, the increase in frequency of abnormal or premature beats, and so forth.

A matching module 165 attempts to match the separated signals with one or more of the stored triggers. If a match is found, the matching module displays the matched corresponding diagnosis through the display module 130, or sends a warning to a healthcare worker or to the patient. Methods such as computer-implemented logic rules, classification trees, expert system rules, statistical or probability analysis, pattern recognition, database queries, artificial intelligence programs and others can be used to match the separated signals with stored triggers.

Figure 1A:
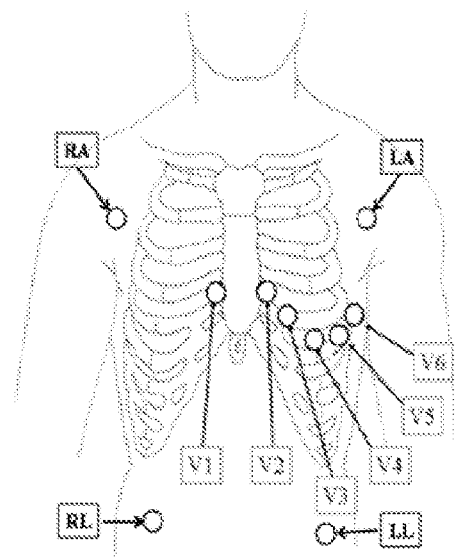
FIG. 1A shows a possible placement pattern for a 12-lead EKG set, according to a disclosed embodiment.

FIG. 1A shows one possible placement pattern for a 12-lead EKG set. In a typical 12-lead set, a grounding pad RL is placed on the patients right leg, and sensor pads LL(aVF), RA(aVR), and LA(aVL) are placed on the patient's left leg, right arm, and left arm, respectively. Six sensor pads are placed on the chest, and are identified as V1-V6. These 9 sensor pads provide 9 lines of unipolar input to the EKG input module. Three bipolar inputs are provided by leads positioned between RA/LA(Lead I), RA/LL(Lead II), and LA/LL (Lead III), respectively. Since the use and placement of EKG leads is well know, it will not be described in detail. Although a 12-lead set has been illustrated, it will be understood that fewer or more sensors or leads may be used.

Figure 2:
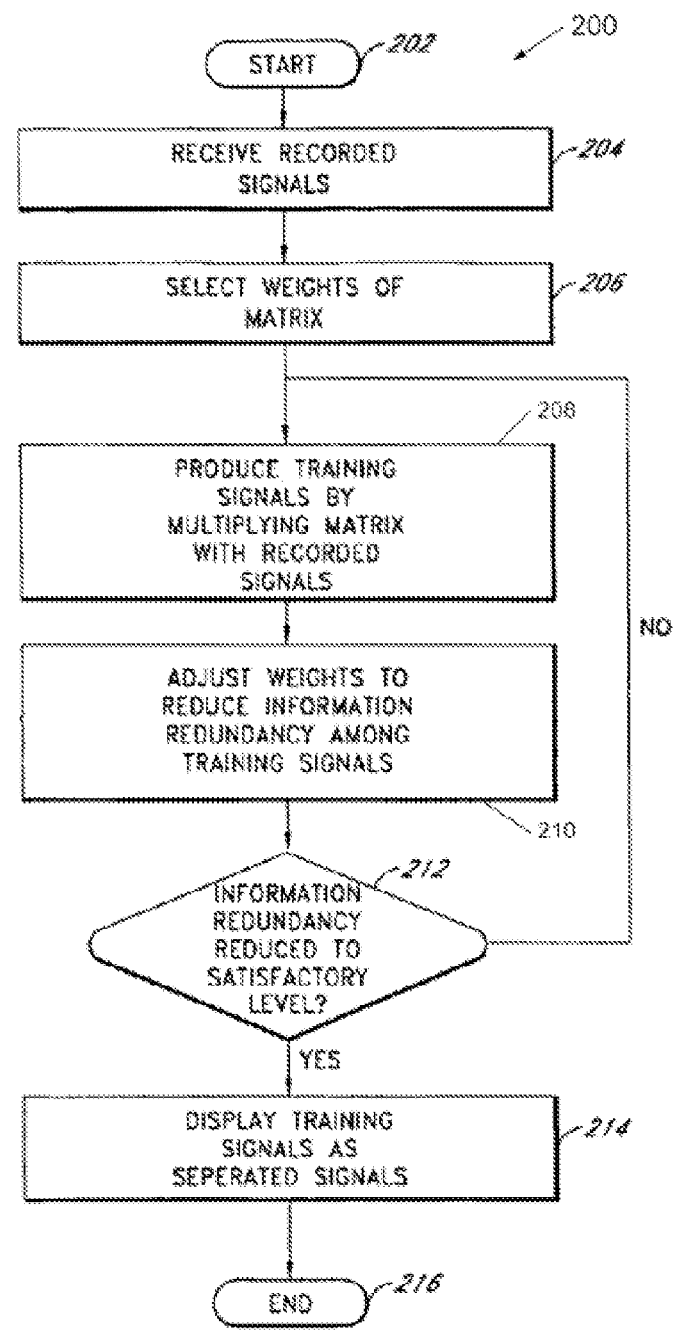
FIG. 2 is a flowchart illustrating one embodiment of a process for separating cardiac signals.

FIG. 2 is a flowchart illustrating one embodiment of a process 200 for separating ECG signals. The process starts from a start block 202, and proceeds to a block 204, where the computing module 120 of the ECG system 100 receives the recorded signals Xj from the electrode sensors, with J being the number of sensors. Prior to processing, the signals can be amplified to strengths suitable for computer processing. Analog-to-digital conversion of signals can also be performed in order to provide the signals in a digitized form.

From the block 204, the process proceeds to a block 206, where the initial values for a "un-mixing" matrix of scaling weights Wij are selected. In one embodiment, the initial values for a matrix of initial weights Wi0 are also selected. The process then proceeds to a block 208, where a plurality of training signals Yi are produced by operating the matrix on the recorded signals. In a preferred embodiment, the training signals are produced by multiplying the matrix with the recorded signals such that Yi=Wij*Xj. In one embodiment, the initial weights Wi0 are included such that Yi=Wij*Xj+Wi0. The process proceeds from the block 208 to a block 210, wherein the scaling weights Wij and optionally the initial weights Wi0 are adjusted to reduce the information redundancy among the training signals.

In some embodiments, a linear mapping, z, is computed from variables, Y, such that the linear mapping, z, is correlated with the desired physiological parameter, such as a blood analyte concentration level.

$$z=WY \qquad \text{Eq. 1}$$

The variables, Y, may comprise non-invasively measured variables that may have been pre-processed, including transforming any Y that is nonlinear. Although the mapping may be substantially insensitive to personal and/or environmental changes, the goal is to have a system that is robust to such changes. Accordingly, the prediction weight, W, may be determined by a variety of methods. For example, test data may be used to establish a linear regression between invasively measured blood analyte concentration levels and the variables Y. However, preferably, a more complex regression model such as a neural network can be used to determine the prediction weight.

In process 200, a source separation process is illustrated to separate an independent signal from at least two data sets. In one example, signal separation process(es) 200 includes signal separation or blind source extraction (BSE) techniques known to those skilled in the art, including non-orthogonal transformation methods. Each input data set is considered a channel of input signals to the transformation. The signal separation method is applied to the channels of input signals to separate a multivariate signal into statistically substantially-independent components. In one specific implementation, a blind source separation (BSS) or an independent component analysis (ICA) or an independent vector analysis (IVA) method is used as the signal separation process. Blind source extraction (BSE) is a techniques that extracts a small subset of source signals from high-dimensional observed signals. See, for example: Cichocki, A., Amari, S., Adaptive Blind Signal and Image Processing: Learning Algorithms and Applications, John Wiley & Sons, New York (2002); Cichocki, A., et al.: A Blind Extraction of Temporally Correlated but Statistically Dependent Acoustic Signals, Proc. of the 2000 IEEE Signal Processing Society Workshop on Neural Networks for Signal Processing X (2000) 455-46; Smith, D., Lukasiak, J., Burnett, I.: Blind Speech Separation Using a Joint Model of Speech Production, IEEE Signal Processing Lett. 12 (11) (2005) 784-787; Zhang, Z.-L., Yi, Z.: Robust Extraction of Specific Signals with Temporal Structure, Neurocomputing 69 (7-9) (2006) 888-893; Barros, A. K., Cichocki, A.: Extraction of Specific Signals with Temporal Structure, Neural Computation 13 (9) (2001) 1995-2003; Cichocki, A., Thawonmas, R.: On-line Algorithm for Blind Signal Extraction of Arbitrarily Distributed, but Temporally Correlated Sources Using Second Order Statistics, Neural Processing Letters 12 (2000) 91-98; Mandic, D. P., Cichocki, A.: An Online Algorithm for Blind Extraction of Sources with Different Dynamical Structures, Proc. of the 4th Int. Conf on Independent Component Analysis and Blind Signal Separation (ICA 2003) (2003) 645-650; Liu, W., Mandic, D. P., Cichocki, A.: A Class of Novel Blind Source Extraction Algorithms Based on a Linear Predictor, Proc. of ISCAS 2005, pp. 3599-3602; Liu, W., Mandic, D. P., Cichocki, A.: Blind Second-order Source Extraction of Instantaneous Noisy Mixtures, IEEE Trans. Circuits Syst. II 53 (9) (2006) 931-935.

Independent component analysis (ICA) is a computational method for separating a multivariate signal into additive subcomponents supposing the mutual statistical independence of the non-Gaussian source signals. It is a special case of blind source separation. The statistical method finds the independent components (aka factors, latent variables or sources) by maximizing the statistical independence of the estimated components. ICA can identify linear subspaces of independent components from the signal. In its simplified form, ICA operates an "un-mixing" matrix of weights on the mixed signals, for example multiplying the matrix with the mixed signals, to produce separated signals. The weights are assigned initial values, and then adjusted to maximize joint entropy of the signals in order to minimize information redundancy. This weight-adjusting and entropy-increasing process is repeated until the information redundancy of the signals is reduced to a minimum. When applied to signal Y, the ICA method may identify a number of subspaces for which signals are independent of each other. More generally, by applying signal separation techniques, linear components can be identified which are independent of each other. Since the invention signal separation techniques can extract original signal from multi-dimensional observation signals mixed with high noise, cleaner signals can be extracted or separated which show higher correlation with the desired physiological parameter. Algorithms for ICA include infomax, FastICA and JADE, but there are many others also.

Although process 200 may use an ICA process, it will be understood that other signal separation processes may be used in accordance with this disclosure, including extensions of ICA. Many different algorithms for solving the separation can be found in the literature, including some of the better known algorithms such as JADE (Cardoso & Souloumiac (1993) IKE proceedings-F, 140(6); SOBI (Belouchrani et al. (1997) IEEE transactions on signal processing 45(2)); BLISS (Clarke, I. J. (1998) EUSIPCO 1998)); Fast ICA (Hyvarinen & Oja (1997) Neural Computation 9:1483-92); and the like. A summary of the most widely used algorithms and techniques can be found in books and references therein about ICA and BSS (e.g., PCT Application Nos. WO 05/052848 and WO 03/073612; Girolami, M., Advances in Independent Component Analysis, Springer (December 2006); Stone, J. V., Independent Component Analysis: A Tutorial Introduction, MIT Press (September 2004); Roberts and Everson, Independent Component Analysis: Principles and Practice, Cambridge University Press (March 2001); Hyvarinen et al., Independent Component Analysis, 1st edition (Wiley-Interscience, May 2001); Haykin, Simon. Unsupervised Adaptive Filtering, Volume 1: Blind Source Separation. Wiley-Interscience; (Mar. 31, 2000); Haykin, Simon. Unsupervised Adaptive Filtering Volume 2: Blind Deconvolution. Wiley-Interscience (March 2005); and Mark Girolami, Self Organizing Neural Networks: Independent Component Analysis and Blind Source Separation (Perspectives in Neural Computing) (Springer Verlag, September 1999). Singular value decomposition algorithms have been disclosed in Adaptive Filter Theory by Simon Haykin (Third Edition, Prentice-Hall (NJ), (1996).

Also contemplated are extensions of ICA developed to allow ICA applicable to a wider range of data analysis area. These extensions include noisy ICA, independent subspace analysis, multidimensional ICA, (post-) nonlinear ICA, tree-dependent component analysis, subband decomposition ICA, independent vector analysis (IVA, PCT Application No. PCT/US2006/007496; U.S. Provisional App. Nos. 60/891,677, 60/777,900 and 60/777,920; Kim et al., Independent Vector Analysis: An Extension of ICA to Multivariate Components. ICA 2006: 165-172; Lee, et al., Complex FastIVA: A Robust Maximum Likelihood Approach of MICA for Convolutive BSS. ICA 2006: 625-632; Taesu Kim, "Independent Vector Analysis," Ph. D. Thesis, KAIST, February, 2007; each incorporated herein by reference).

Other non-orthogonal transformation methods contemplated for source separation, such as oblique Procrustean transformation, factor analysis, independent factor analysis, Promax, variational methods and so forth, can also be used.

The process 200 proceeds to a decision block 212, where the process determines whether the information redundancy has been decomposed to a satisfactory level. If the process determines that information redundancy among the training signals has been reduced to a satisfactory level, then the process proceeds to a block 214, where the training signals are displayed as separated signals Yi, with i being the number of components for the separated signals. In a preferred embodiment, i, the number of components of separated signals, is equal to j, the number of channels of recorded signals. Otherwise the process returns from the block 212 to a block 213 to again adjust the weights. From the block 213, the process returns to block 208 to produce additional training signals.

For the un-mixing matrix W with the final weight values, its rows represent the time courses of relative strengths/activity levels (and relative polarities) of the respective separated components. Its weights give the surface topography of each component, and provide evidence for the components' physiological origins. For the inverse of matrix W, its columns represent the relative projection strengths (and relative polarities) of the respective separated components onto the channels of recorded signals. The back projection of the ith independent component onto the recorded signal channels is given by the outer product of the ith row of the separated signals matrix with the ith column of the inverse un-mixing matrix, and is in the original recorded signals. Thus cardiac dynamics or activities of interest accounted for by single or by multiple components can be obtained by projecting one or more ICA components back onto the recorded signals, $X=W-1*Y$, where Y is the matrix of separated signals, $Y=W*X$.

The separated signals are determined by the ICA method to be statistically independent and are presumed to be from independent sources. Regardless of whether there is in fact some dependence between the separated ECG signals, the separated signals provide a beneficial perspective for physicians to detect and to locate the abnormal heart conditions of a patient.

In one embodiment, time-delay between source signals is ignored. Since the sampling frequencies of cardiac signals are in the relatively low 200-500 Hz range, the effect of time-delay can be neglected.

Improved methods of ICA can be used to speed up the signal separation process. In one embodiment, a generalized Gaussian mixture model is used to classify the recorded signals into mutually exclusive classes. The classification methods have been disclosed in U.S. Pat. No. 6,424,960 titled "Unsupervised adaptation and classification of multiple classes and sources in blind source separation." In another embodiment, the computing module 120 incorporates a priori knowledge of cardiac dynamics, for example supposing separated QRS components to be highly kurkotic and (ar)rhythmic component(s) to be sub-Gaussian. ICA methods with incorporated a priori knowledge have been disclosed in T-W. Lee, M. Girolami and T. J. Sejnowski, Independent Component Analysis using an Extended Infomax Algorithm for Mixed Sub-Gaussian and Super-Gaussian Sources, Neural Computation, 1999, Vol. 11(2): 417-441, and M. Girolami, An alternative perspective on adaptive independent component analysis algorithms. Neural Computation, 1998, Vol. 10:2103-2114; Fixed number ICA algorithm by Apo (commonly referred to as "fastICA"); ICA based on Negentropy; ICA by Cardoso, and JADE, as previously referenced.

Figure 3A:
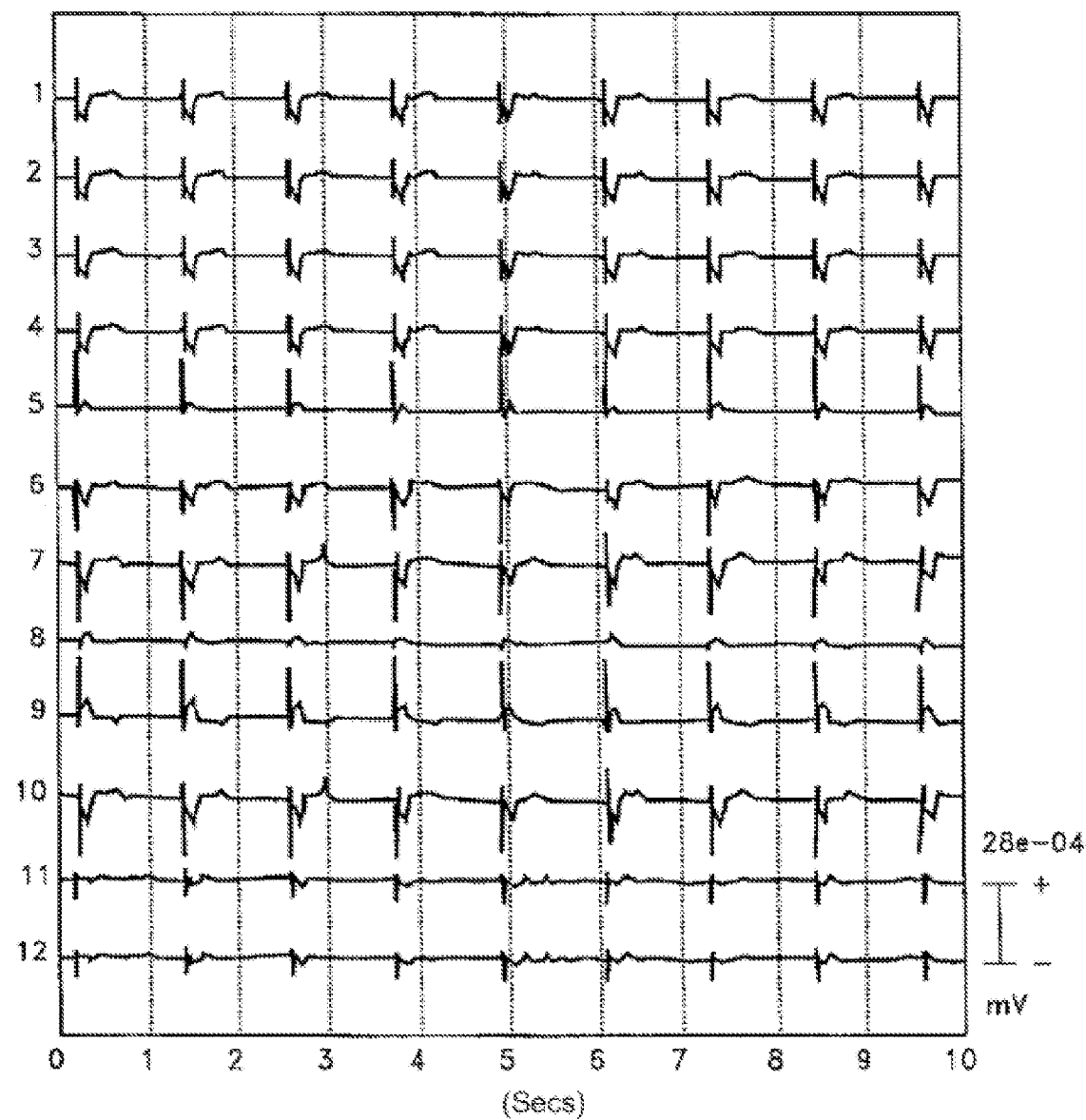
FIG. 3A is a sample chart of recorded ECG signals.

FIG. 3A illustrates a ten-second portion of 12 channels (leads) of signals that were gathered as part of an ECG recording from a patient. The horizontal axis in FIG. 3A represents time progression of ten seconds. The vertical axis represents channel numbers 1 to 12. In a standard 12-lead arrangement, leads II, III and AvF represent signals from the inferior region of the heart. Leads V1, V2 represent signals from the septal region. Leads V5, V6, I, and a VL represent signals from the lateral heart. Right and posterior heart regions typically require special lead placement for recording. To better identify the location of a heart condition, more than 12 leads can be used. For example, 20, 30, 40, 50, or even hundreds of sensors can be placed on various portions of a patient's torso. Fewer than 12 leads can also be used. For example, in one embodiment, 1, 2, 3, 4, 5, 6, 7, 8, 9, 10 or 11 leads may be used. The sensors are preferably non-invasive sensors located on the patient's body surface, but invasive sensors can also be used, or minimally invasive sensors such as typically seen with dry sensors.

The signals of FIG. 3A are, in this case, from a patient that provided a mixture of multiple signals, including QRS complex signals, pacemaker signals, multiple oscillatory activity signals, and background noise. However, because these signals were all occurring simultaneously, they are difficult to separate from one another using conventional ECG technology.

Figure 3B:
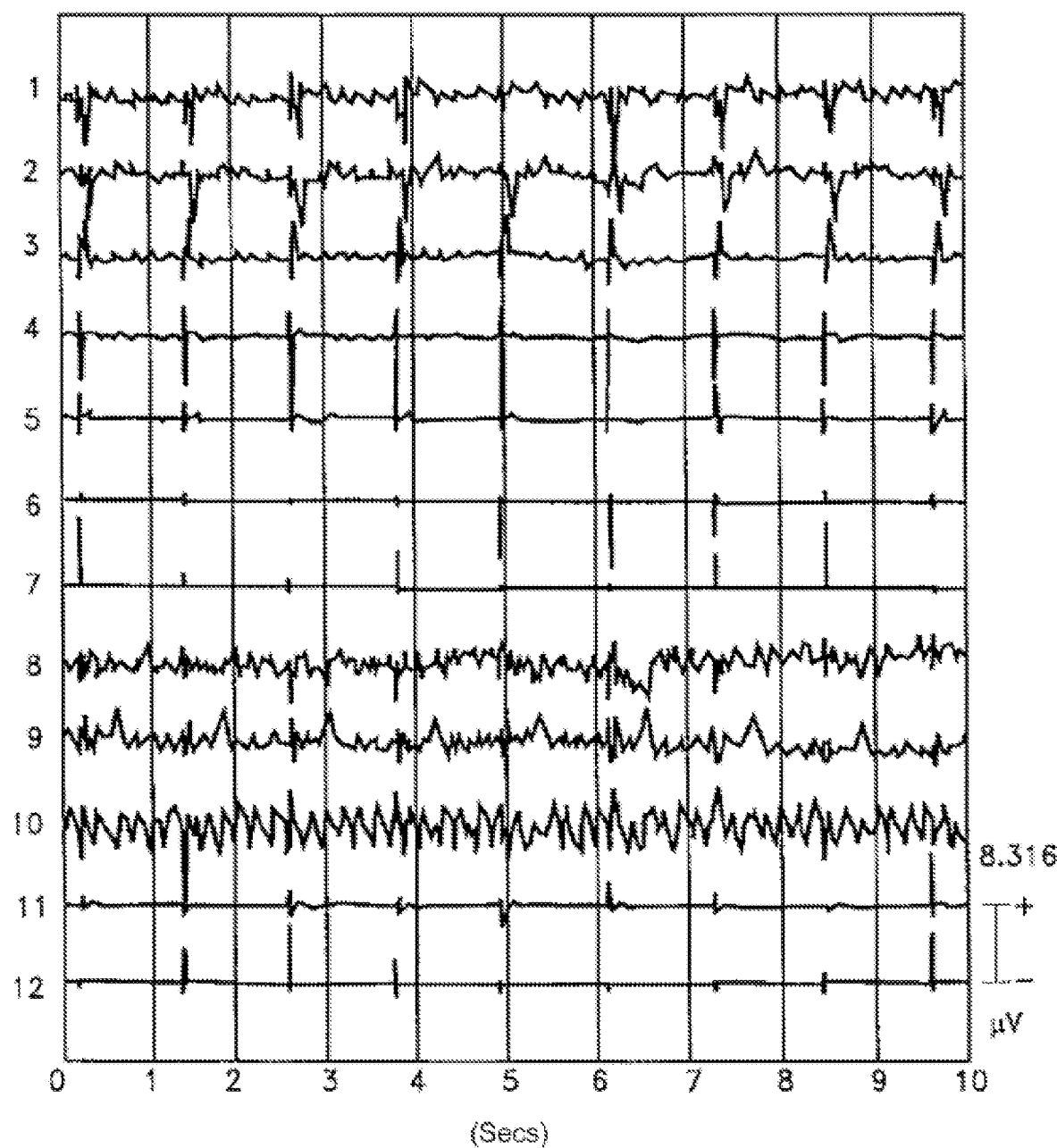
FIG. 3B is a sample chart of separated ECG signals.

In contrast, FIG. 3B illustrates output signals separated from the mixture signals of FIG. 3A, according to one embodiment of the present invention. As above, the horizontal axis in FIG. 3B represents time progression of ten seconds and the vertical axis represents the separated components 1 to 12. The separated signals in FIG. 3B are displayed as components 1 to 12. Each component is a linear combination of one or more leads of recorded ECG signals.

In one embodiment, the 12 leads of recorded ECG signals and the separated components are both displayed, so that a physician can compare the recorded signals against the separated components. The scaling weights for each component can also be displayed, so that the physician can evaluate the composition of a component. For example, if a separated component is a linear combination of 70% of recorded lead #1 signals, 20% of recorded lead #2 signals and 10% of recorded lead #5 signals (the scaling weights 0.7, 0.2 and 0.1 are from the weight matrix produced by the ICA method), the physician may consider the separated component as mainly corresponding to lead #1, and consider the sensor location of lead #1 as the approximate location of the condition represented by the separated component.

As shown in FIG. 3B, the component #1 mainly represents the pacemaker signals and the early part of QRS complex signals. The component #2 mainly represents major portions of later parts of the QRS complex signals. QRS complex signals represent the depolarization of the left ventricle. The component #10 mainly represents atrial fibrillation (a type of arrhythmia) signals. Although components #1 and #10 contain similar frequency contents of oscillatory activity between heartbeats, they capture activities from different spatial locations of the heart.

It was discovered that the signals separated using ICA are usually more independent from each other and have less information redundancy than signals that have not been processed through ICA. Compared to the recorded signals, the separated signals usually better represent the signals from the original sources of the patient's heart. In addition to arrhythmia, the separated cardiac signals can also be used to help detect other heart conditions. For example, the separated signals especially the separated QRS complex signals can be used to detect premature ventricular contraction. The separated signals, especially the separated Q wave signals, can be used to detect myocardial infarction. Separating the ECG signals, especially separating the ST segments between the QRS complex and T wave signals, can help distinguish left and right bundle branch block (LBBB and RBBB), because the abnormal signals for LBBB and RBBB originate from different locations.

Of course, the disclosed system and method are not limited to detecting arrhythmia, or any particular type of disease state. Embodiments of the invention include all methods of analyzing medical signals using ICA. For example, when a pregnant woman undergoes ECG recording, the heart signals from the woman and from the fetus(es) can be separated.

The separated cardiac signals can be characterized as non-random but not easily deterministic, which make them suitable for further analysis, such post-processing techniques such as chaotic analysis. Chaos theory (also called nonlinear dynamics) studies patterns that are not completely random but cannot be determined by simple formulas. The separated signals can be plotted to produce a chaos phase space portrait. By reviewing the patterns in the phase space portrait, including the existence and location of one or more attractors, a user is able to assess the likelihood of abnormality in the signals, which indicate disease conditions in the patient.

In a preferred embodiment, the QRS complex signals are separated into three different components, with each component representing a portion of the QRS complex. The 3 components are 3 data sets that are found to be temporally statistically independent using independent component analysis. Using the three components, a 3-dimensional phase space portrait of QRS complex can be displayed to show the trajectory of the three components.

Figure 3C:
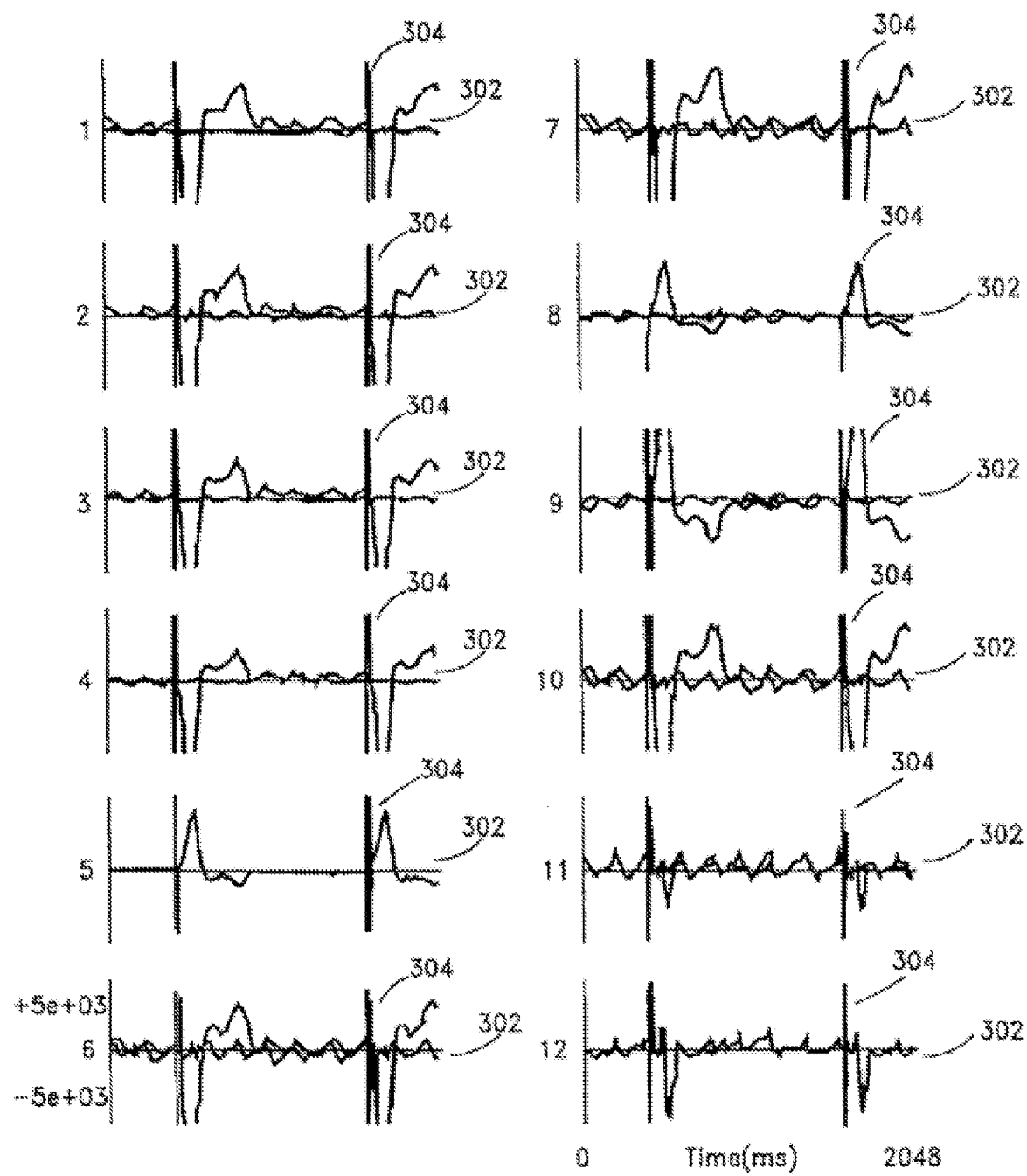
FIG. 3C is a sample chart of one component of separated signals back projected on the recorded signals.

FIG. 3C is a sample chart of the component #10 of separated signals (as shown in FIG. 3B) back projected onto the recorded signals of FIG. 3A. The separated signals of component #10, which indicate arrhythmia, is identified by reference number 302 in FIG. 3C. The 12 channels of recorded signals are identified by reference number 304 for ease of identification. FIG. 3C therefore allows direct visual comparison of a separated component against channels of recorded signals. The back projections of cardiac dynamics allow examination of the amount of information accounted for by single or by multiple components in the recorded signals and to confirm the components' physiological meanings suggested by the surface topography (the aforementioned inverse of columns of the un-mixing matrix).

Figure 4A:
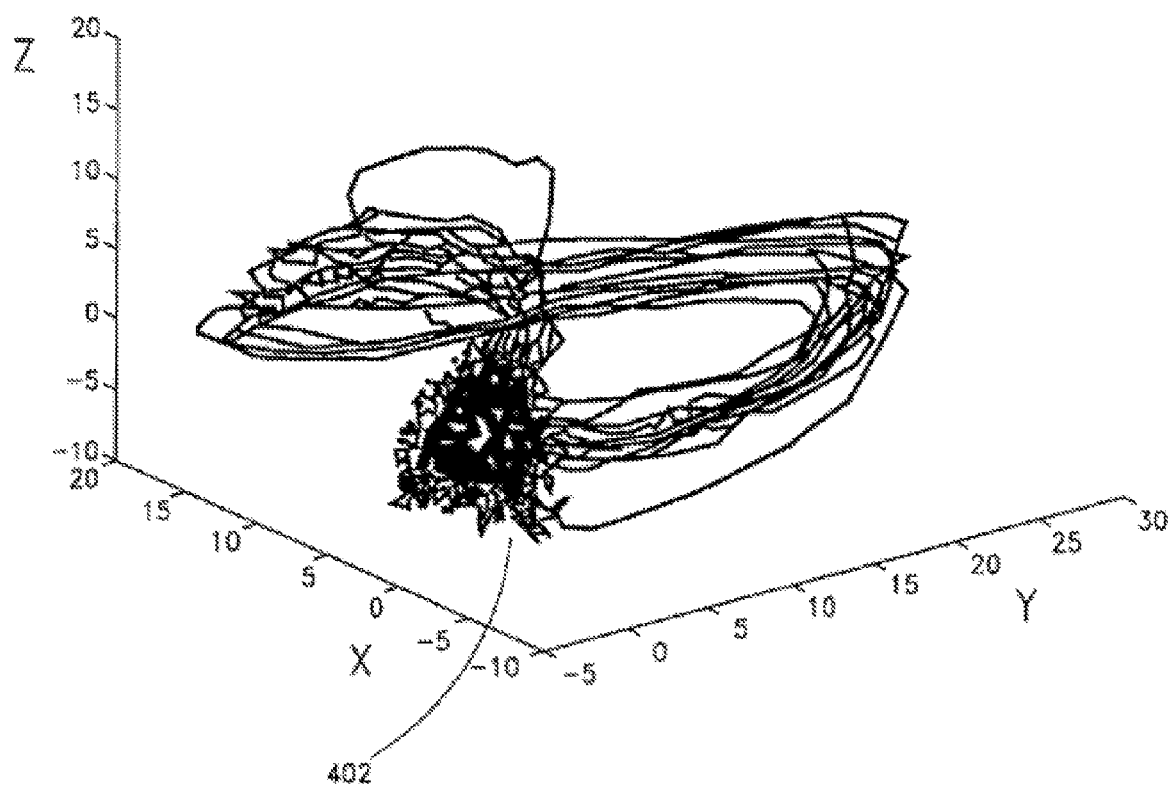
FIG. 4A is a chaos phase space portrait of three components of separated ECG signals of a healthy subject.
Figure 4B:
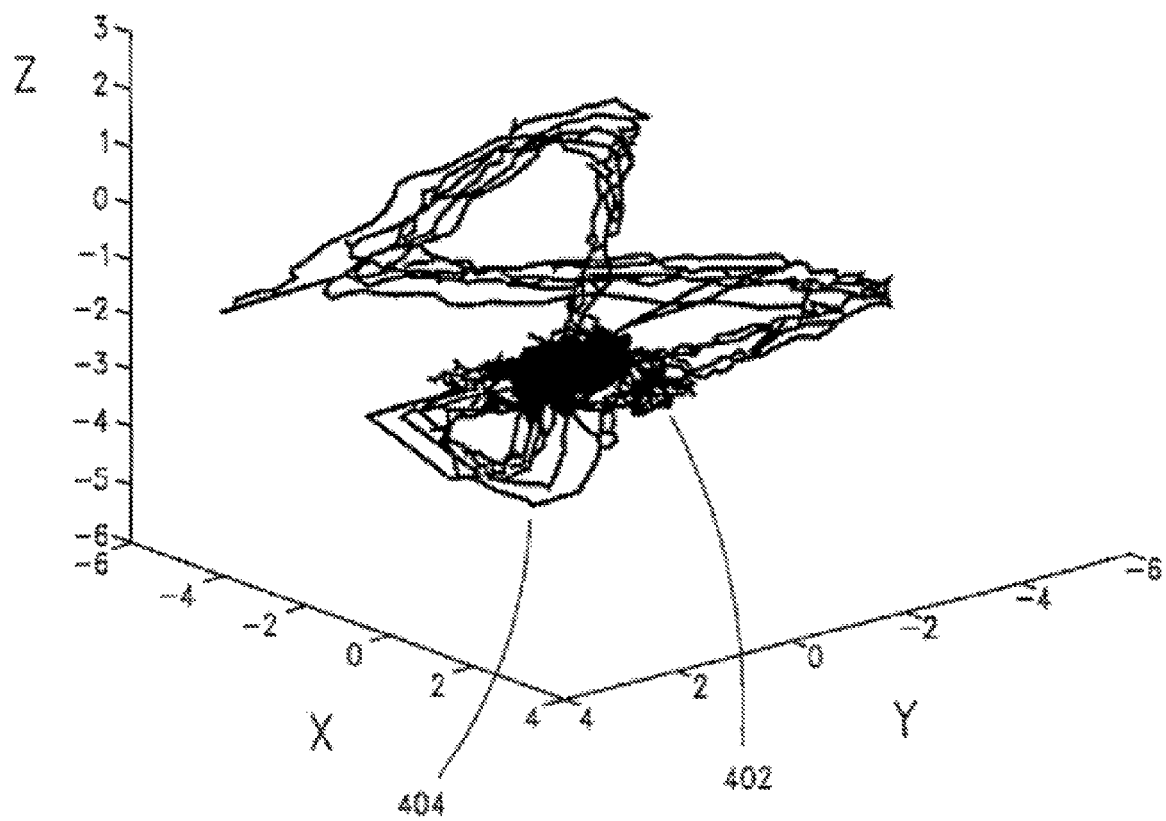
FIG. 4B is a chaos phase space portrait of three components of separated ECG signals of a subject with an abnormal heart condition.

FIG. 4A illustrates the phase space portrait of the ECG recording of a healthy subject. FIG. 4B illustrates the phase space portrait of the ECG recording of an atrial fibrillation patient. In FIGS. 4A and 4B, the x, y, and z axis represent the amplitudes of the 3 QRS components. The separated signals' values over time are plotted to produce the phase space portraits. In the healthy ECG recording of FIG. 4A, the dense cluster 402 indicates the existence of an attractor that attracts the signal values to the region of the dense cluster 402. The dense cluster 402 represents the most frequent occurrences of the signals. In the atrial fibrillation patient ECG recording of FIG. 4B, an additional loop 404, which is not part of the dense cluster 402, is below the attractor and the dense cluster 402 and closer to the base plane than the dense cluster 402. This additional loop 404 is presumably due to the oscillatory activity in the baseline portions of the ECG signals from the atrial fibrillation. The separated component #10 signal that indicates an arrhythmia condition is presumably responsible for the additional loop 404. The visual pattern can be compared with the visual pattern of a health subject and manually recognized as probative of indicating an abnormal condition, such as atrial fibrillation.

Instead of the 3 QRS complex components as shown in FIG. 4B, other components or more than 3 components can also be used to plot the chaos phase space portrait. If more than 3 components are used, the different components can be plotted in different colors. The 3 QRS complex components of FIG. 4B are selected because test results suggest that such a phase space portrait is physiological significant and functions usually well as an indication of a patient's heart condition.

Although FIGS. 3A, 3B, 4A and 4B were produced using test results related to the detection and localization of focal atrial fibrillation, the disclosed systems and methods can and has been used to detect, characterize and/or to localize other heart conditions including arrhythmia, cardiogenic shock, cardiomyopathy, coronary artery disease, endocarditis, valvular regurgitation or other valvular disorder, stenosis, angina, heart attack (myocardial infarction), heart failure, hypertension, or other conditions. The disclosed systems and methods can also be used to detect and to localize focal and re-entrant arrhythmia, paroxysmal atrial fibrillation as well as persistent and chronic atrial fibrillation.

It will be understood that other post-processing, display, or analytic steps may be advantageously used. For example, triggers can also be applied to compare extracted signals and known abnormalities. There has been disclosure of cardiac rhythm management systems that store a list of triggers. U.S. Pat. No. 6,400,982 entitled "Cardiac rhythm management system with arrhythmia prediction and prevention" discloses such a system. If a trigger matches detected cardiac signals from a patient, the system calculates the probability of arrhythmia and activates a prevention therapy to the patient. However the cardiac signals are in fact mixtures of signals from multiple sources, and the signals that are important for arrhythmia detection can be masked by other signals. It is therefore desirable to separate the cardiac signals used in the cardiac rhythm management systems. It will also be understood that spatial pattern matching may be used as in post processing. In spatial pattern matching, a surface map may be generated that allows for selecting and emphasizing specific locations, for example, identifying high activations in the atrium or ventricle.

The disclosed methods can be used to improve existing cardioverter/defibrillators (e.g., AED, ICD and the like) that can deliver electrical stimuli to the heart. In addition to existing ICD's and existing pacemakers, some of the existing cardiac rhythm management devices also combine the functions of AEDs, pacemakers and ICD's. A computing module embodying the disclosed methods can be added to the existing systems to separate the recorded cardiac signals. The separated signals are then used by the cardiac rhythm management systems to detect or to predict abnormal conditions. Upon detection or prediction, the cardiac rhythm management system would automatically treat the patient, for example by delivering pharmacologic agents, pacing the heart in a particular mode, delivering cardioversion/defibrillation shocks to the heart, or neural stimulation of the sympathetic or parasympathetic branches of the autonomic nervous system. Instead of, or in addition to, automatic treatment, the system can also issue a warning to a physician, a nurse or the patient. The warning can be issued in the form of an audio signal, a radio signal, and so forth. The disclosed signal separation methods can be used in cardiac rhythm management systems in hospitals, in patient's homes or nursing homes, or in ambulances. The cardiac rhythm management systems include automated external defibrillators, implantable cardioverter defibrillators, pacemakers, biventricular or other multi-site coordination devices and other systems for diagnostic ECG processing and analysis. The cardiac rhythm management systems also include automatic external defibrillators and other external monitors, programmers and recorders.

In one embodiment, an improved cardiac rhythm management system includes a storage module that stores the separated signals. In one arrangement, the storage module is removable from the cardiac rhythm management system and connected to a computing device. In another arrangement, the storage module directly connects to a computing device without being removed from the cardiac rhythm management system. The computing device can provide further analysis of the separated signals, for example displaying a chaos phase space portrait using some of the separated signals. The computing device can also store the separated signals to provide a history of the patient's cardiac signals.

The disclosed methods can also be applied to predict the occurrence of arrhythmia within a patient's heart. After separating recorded ECG signals into separated signals, the separated signals can be matched with stored triggers and diagnosis as described above. If the separated signals match stored triggers that are associated with arrhythmia, an occurrence of arrhythmia is predicted. In other embodiments, an arrhythmia probability is then calculated, for example based on how closely the separated signals match the stored triggers, based on records of how frequently in the past has the patient's separated signals matched the stored triggers, and/or based on how frequently in the past the patient has actually suffered arrhythmia. The calculated probability can then be used to predict when will the next arrhythmia occur for the patient. Based on statistics and clinical data, calculated probabilities can be associated with specified time periods within an arrhythmia will occur.

In addition to ECG signals, the disclosed systems and methods can be applied to separate other electrical signals such as electroencephalogram signals, electromyographic signals, electrodermographic signals, and electroneurographic signals. They can be applied to separate other types of signals, such as sonic signals, optic signals, pressure signals, magnetic signals and chemical signals. The disclosed systems and methods can be applied to separate signals from internal sources, for example within a cardiac chamber, within a blood vessel, and so forth. The disclosed systems and methods can be applied to separate signals from external sources such as the skin surface or away from the body. They can also be applied to record and to separate signals from animal subjects.

Figure 5:
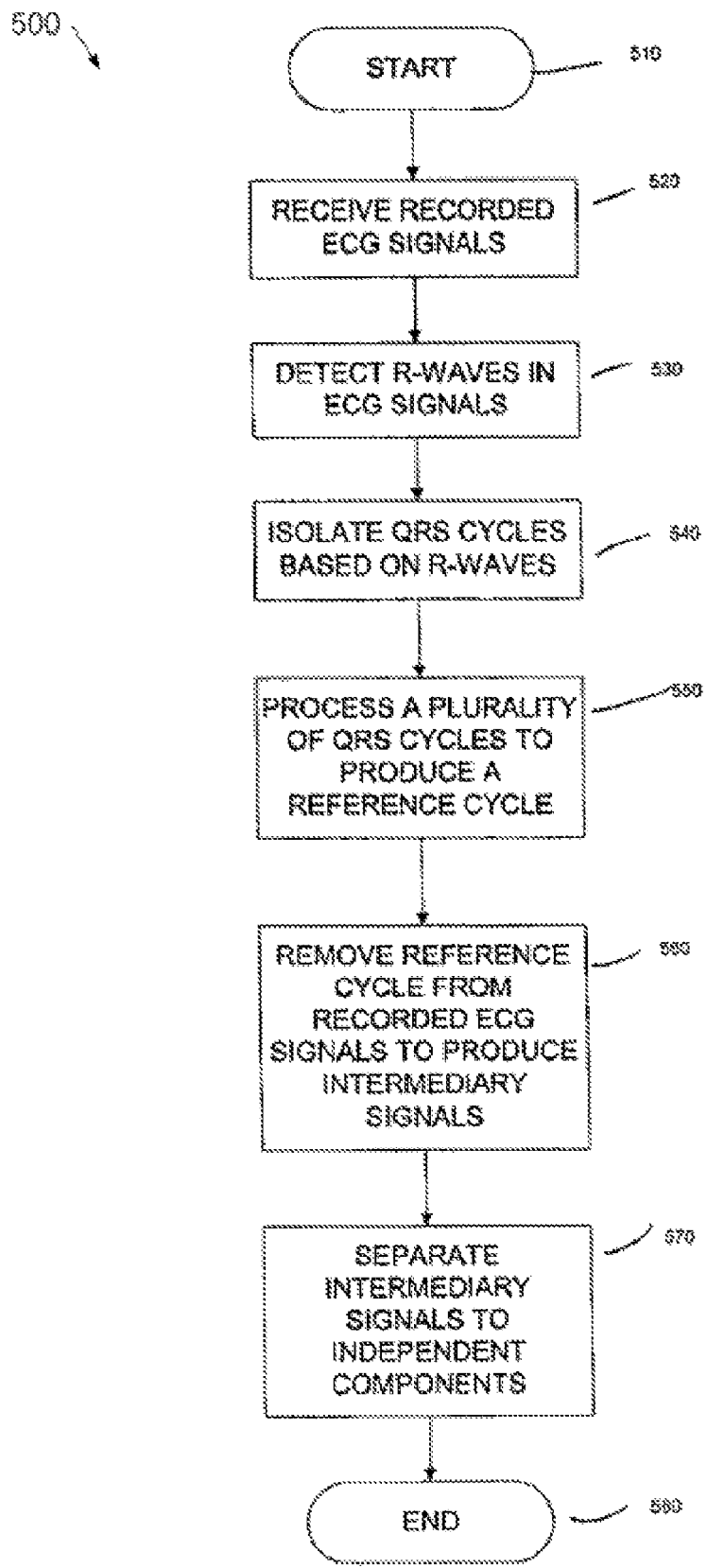
FIG. 5 is a flowchart illustrating one embodiment of a process of using ICA to separate 3-lead cardiac signals.

FIG. 5 is a flowchart illustrating an additional embodiment of a process 500 of using ICA to separate cardiac signals. In this embodiment, one or more data sets are pre-processed. As employed herein, pre-processing comprises preparing the input data (signals or information) for signal separation processing. In some embodiments, pre-processing is not necessary. The pre-processing may include a variety of processes, including identifying, categorizing, filtering, transforming, calibrating, resampling, smoothing, transforming, normalizing, selecting, registration, quantization, and other similar processes, individually or in combination, such that extraneous information is removed while relevant information is not lost. Preferably, the pre-processing step will remove or substantially attenuate extraneous information without distorting the relevant information. Although such step may impact the relevant information, the preferred embodiment errs on preserving or potentially preserving the characteristics of the desirable or relevant information. Accordingly, the pre-processing step retains as much relevant or potentially relevant information as possible, contrary to steps such as certain normalizing or averaging techniques, or other processes which remove information. For example, principal components analysis (PCA) is a technique for simplifying a data set by reducing multidimensional data sets to lower dimensions for analysis. Although such steps simplify processing, information which is important or potentially important is permanently lost. Pre-processing may be performed on each data set or an aggregate set of data.

Preferably, the pre-processing step or steps involves identifying and/or categorizing input information to determine whether further pre-processing is required. Information which identifies the input data sets as non-activity or static or null information, duplication, non-linearity, or other such characterization would improve processing. Filters can include high-pass or low pass filters to remove extreme or relatively extreme low frequency or high frequency signals, respectively. Filtering can include filters on each data signal or on the aggregate of signals, such as removal of non-relevant inputs. Pre-processing may be static or adaptive. For example, the output of the separation signal may influence the pre-processing step as a feed forward or feedback loop, or alternatively, the filter can be designed learned filters from prior knowledge or empirical data acquisition. Pre-processing may also include the combining of two or more measurements. For example, two or more readings may be combined into a single variable if they are identical.

One embodiment of the invention comprises the process 500 to first "remove" the QRS complex from the recorded cardiac signals. In some diagnostic evaluations, the QRS signal is extraneous, and may dominate received signals to block or mask important other sources. Although this example used the QRS signal as the extraneous signal, it will be appreciated that other extraneous signals may be removed. As discussed previously, the QRS complex typically dominates measured cardiac signals, especially when only a few leads are used, e.g., 2 or 3. By removing the QRS complex from the recorded signals, the remaining cardiac signals can more accurately be separated into their individual components. Thus, once the QRS complex is removed from the ECG signals, the remaining cardiac signals are separated into statistically independent components using an ICA method.

As shown in FIG. 5, from a start block 510, the process 500 proceeds to a block 520, where the recorded ECG signals are received. The received ECG signals are preferably recorded over a continuous time period, such as 1-30 seconds, 1 minute, 10 minutes, or more. The process 500 then proceeds to a block 530 to detect one or more characteristics of each signal cycle. As is well known to those skilled in the art, recorded cardiac signals include cycles of substantially repeating heartbeat signals and QRS complex waves. For example, as shown in FIG. 7A, a 10-second portion of recorded ECG signals represents 11 heartbeat cycles and QRS complex cycles, with each of the QRS complex cycles having a peak R-wave. Over a continuous time period, the heartbeat signals and QRS complex wave signals repeat over cycles, with typically small variations. Referring back to FIG. 5, at the block 530, the process 500 detects specific characteristics of each cycle. For example, in one embodiment, the process 500 detects the position of R-waves in the recorded ECG signals. Since QRS complex waves are typically dominant in recorded ECG signals and typically repeat in substantially regular cycles, the recorded ECG signals are preferably isolated into QRS complex cycles. Since R-waves typically represent the highest points in QRS complex cycles, R-wave detection is a preferred way of identifying QRS complex cycles.

In one embodiment, R-waves are detected within each cycle by calculating the correlation between recorded ECG signals and a triangle template. The triangle template can be represented by a matrix d such as d=[0 0 0 1 3 5 3 1 0 0 0] with N time points. N represents the number of time units in the triangle template, for example the number of seconds in the triangle template. The following formula $$r = \frac{\frac{\sum_i (x_i - \bar{x})(d_i - \bar{d})}{N}}{\sqrt{\frac{\sum_i (d_i - \bar{d})^2}{N}} \sqrt{\frac{\sum_i (x_i - \bar{x})^2}{N}}}$$

is used to calculate the correlation between the recorded ECG signals and the triangle template. In the equation above, $x_i$ represents the recorded ECG signal at time point i, r represents the correlation coefficient between the recorded ECG signals and the triangle template. For the recorded ECG signals over M continuous time points, correlation coefficients rj are calculated with j=1, . . . , M. With the correlation coefficients plotted over the M continuous time points, the coefficients achieve peak values at time points near the occurrence of R-waves. The correlation coefficients over the M time points, which correspond to the recorded ECG signals over the M time points, are then searched to detect the location of R-waves.

A minimum correlation coefficient threshold value can be used to limit the search area over the M time points. In one embodiment, with correlation coefficient values in the range between 0 and 1, only the subsections where the correlation coefficients are greater than a minimum threshold of 0.6 are searched for R-wave detection. The insignificant subsections with coefficients less than or equal to 0.6 are thus eliminated. The plotted correlation coefficients and corresponding recorded ECG signals over M continuous time points are thus separated into a number of subsections, with each subsection having correlation coefficient values greater than the threshold value. For every subsection of the recorded ECG signals, the local maximum is identified as the R-wave peak point. In another embodiment, each point above a certain correlation coefficient value, such as 0.8 or 0.9, is identified as a R-wave peak point.

Other methods can also be used to detect R-waves. For example, instead of a simple triangle template, a more complex template, such as a template formed as a linear mixture of multiple triangle waves, can also be used. Instead of detecting R-waves, other waves, for example P-waves, Q-waves, ST segments or the combinations of a Q-wave and a R-wave, can also be detected for the purpose of isolating QRS cycles in recorded ECG signals.

As described above, R-wave detection is one way of identifying QRS cycles in recorded ECG signals. However, in some circumstances, identification of the R-wave may not be the preferred method for identifying QRS complexes. For example, in some diseases, such as left bundle branch block and right bundle branch block, large variations in the QRS cycle times may be apparent. With large variations of QRS complex cycle times in recorded ECG signals, R-wave detection may not be the desirable way of identifying the QRS complex in each cycle. Other methods, such as wavelet transformation, can be used to produce a reference cycle from a continuously recorded series of ECG signals. The reference cycle may include substantially the characteristics of an "average" cycle of the recorded ECG signals. In addition, the reference cycle frequency is preferably identical or similar to a heartbeat cycle frequency.

The algorithms in the relevant art adapt a range of different approaches to yield a procedure leading to the identification of the waves under consideration. These approaches are mainly based on derivative-based techniques [Afonso et al., IEEE Trans. Biomed. Eng., (1999) 46:192-202; Fraden and Neumann, Med. Biol. Eng. Comput., (1980) 18:125-132; Holsinger et al., IEEE Trans. Biomed. Eng., (1971) 18:121-217], classical digital filtering [Fischer et al., Magn. Reson. Med., (1999) 42(2):361-70; Keselbrener et al., Med. Eng. Phys., (1997) 19(5):481-484; Leski and Tkacz, Proc. 14th Annu. Int. Conf IEEE Eng. in Med. and Bio. Soc., Part 2, Paris, France, pp. 555-556, 1992; N. V. Thakor, Biomed. Sci. Instrum., (1978) 14:62-72; W. J. Tompkins, Comput. Programs Biomed., (1978) 8(1):16-28; W. J. Tompkins, Biomed. Sci. Instrum., (1978) 14: 61-66], adaptive filtering [Proc. 9th Annu. Conf IEEE Engineering in Medicine and Biology Society, Boston Mass., 13-16 pp. 1885-1886 1987; Lin and Chang, IEEE Trans. Biomed. Eng., (1989) 36:1050-1055], wavelets [Bahoura et al., Comput. Methods Programs Biomed., vol. 52, no. 1, pp. 35-44, 1997; Di-Virgilio et al., 1995 IEEE Eng. Med. Biol. 17th Ann. Conf, 21st Canadian Med. Biol. Eng. Conf, Montreal, Canada, (1997); Kadambe et al., IEEE Trans. Biomed. Eng., (1999) 46:838-848; Zheng, and Tai, IEEE Trans. Biomed. Eng., (1995) 42:21-28], neural networks [Strintzis et al., Neural Netw. World, (1992) 3(6): 477-484, and Xue et al., IEEE Trans. Biomed. Eng., (1992) 39:317-329], hidden Markov models [Coast et al., IEEE Trans. Biomed. Eng., (1990) 37:826-836], mathematical morphology [P. E. Trahanias, Biomedical Engineering, IEEE Transactions, (1993) 40(2):201-205], genetic algorithms [Poli, et al., IEEE Trans. Biomed. Eng., (1995) 42:1137-1141], Hilbert Transform [Nygards and Srnmo, Med. Biol. Eng. Comput., (1983) 21, and Zhou et al., Proc. 10th Annu. Int. Conf, IEEE Engineering in Medicine and Biology Society, New Orleans, La., (1988)], syntactic methods [E. Skordalakis, Pattern Recognition., (1986) 19(4):305-313], maximum a posteriori estimation [Borjesson et al., IEEE Trans. Biomed. Eng., (1982) 29:341-351] and zero-crossing-based identification techniques [Kohler et al., Engineering in Medicine and Biology Magazine, IEEE, (2002) 21:42-57]. See, also generally, Acharya & Suri, Advances in Cardiac Signal Processing, (Springer Verlag, 2007).

Still referring to FIG. 5, after the position of the indicator of the QRS complex, such as the R-wave, has been identified within each cycle, the process 500 proceeds to a block 540 to isolate the QRS signals from a plurality of the detected cycles. For example, for a 60-second series of recorded ECG signals, the process 500 detects the positions of the R-waves within each cycle and thereafter isolates the positions of the QRS complexes within each cycle from the recorded signals. In one embodiment, the process 500 calculates the time interval between two adjacent detected R-waves, and isolates QRS complex cycles based on the calculated time intervals. For example, if the time interval between two adjacent detected R-waves is 800 ms, the process 500 isolates a QRS complex cycle as starting at 400 ms before a detected R-wave and ending at 400 ms after the detected R-wave. The process 500 may also isolate a signal cycle as, for example, starting at 600 ms before a detected R-wave and ending at 200 ms after the detected R-wave. In other embodiments, in order to take into account the heart rate variability over time, the process 500 calculates the time interval between pairs of adjacent detected R-waves, and calculates the average or mean time interval between two adjacent R-waves. In yet another embodiment, the process 500 calculates the total time interval T between a first detect R-wave and an n-th detected R-wave, and calculates the time interval $T/(n-1)$ as the average time interval between two adjacent R-waves. The process 500 then isolates signal cycles based on the average or mean time interval.

For patients with certain abnormal medical conditions, the recorded ECG signals may include some heartbeat cycles with difficult-to-detect R-waves. These heartbeat cycles can be omitted from the isolated cycles. For example, with a heartbeat rate determined at 800 ms, a heartbeat cycle can be isolated as starting at 400 ms before a detected R-wave and ending at 400 ms after the detected R-wave. Cycles without detected R-waves are thus omitted.

From the block 540, the process 500 proceeds to a block 550 to produce a reference QRS signal based on the isolated cycles. In one embodiment, the process 500 computes the reference QRS signal based on an average, or a mean, of the plurality of isolated QRS cycle signals. This average is calculated as the average shape and size of a QRS complex from the recorded cardiac signals.

The process 500 then proceeds from the block 550 to a block 560, wherein the reference cycle signals are removed from the recorded ECG signals to produce intermediary signals. Accordingly, the "reference" QRS complex signal is thereby removed from each of the recorded cycles. In one embodiment, for example, a regression method or a match filter is used to remove the reference cycle signals from the recorded ECG signals. The intermediary signals thus have substantially removed the dominating QRS waves, but still retain other information that may indicate medical conditions. It should be noted that the intermediary signals may still include some remaining portions of QRS complex signals, since removing the reference cycles from the recorded ECG signals does not always remove all QRS complex signals. In addition the overall scale of the reference QRS signal can be matched to the scale of the recorded QRS signal within each cycle prior to removal of the QRS signal. This allows for instances where there is variation in the scale of the QRS complex during differing cycles. Once the QRS reference signal has been removed, these complex signals no longer dominate the intermediary signals.

The process 500 then proceeds to a block 570, where a non-orthogonal transformation method such as an ICA method is used to separate the intermediary signals into statistically substantially independent components. For example, filters with weight matrixes are applied to the 3 channels of intermediary signals to produce as output linear combinations of the 3 channels of signals, and the matrixes are updated in iterations to continuously reduce the information redundancy among the channels. The number of independent components can be equal to or different from the number of leads. Other non-orthogonal transformation methods, such as Varimax, Promax, and so forth, can also be used. The separated signals are then displayed on an electronic screen, stored in a computer, or printed on paper to be used by a physician to study the medical conditions of the patient. The process 500 terminates at an end block 580. The separated signals can also be used for automated monitoring and prevention therapy activation.

Figure 6:
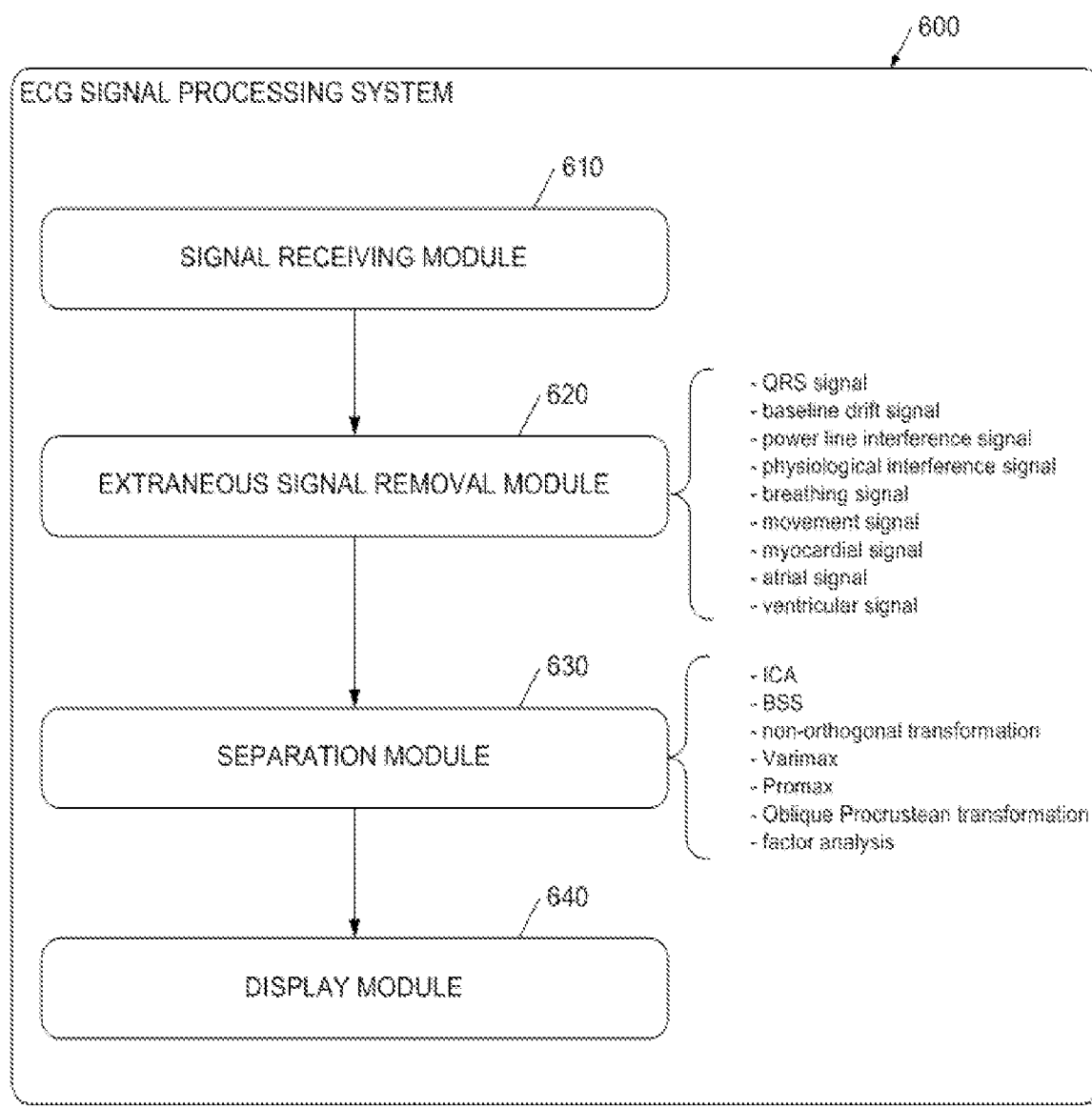
FIG. 6 is a diagram illustrating one embodiment of a system adapted to separate 3-lead cardiac signals.

FIG. 6 is a diagram illustrating one embodiment of a system adapted to separate cardiac signals. The ECG signal processing system 600 includes a signal receiving module 610, an extraneous signal removal module 620, a separation module 630, and a display module 640. The signal receiving module 610 receives a series of recorded ECG signals. In one embodiment, the receiving module 610 receives ECG signals stored on a Holter device. The extraneous signal removal module 620 substantially removes one or more selected extraneous signals from the received signals to produce intermediary signals. For example, the extraneous signal may be the dominant QRS signal. In other cases, the extraneous signal may be a baseline drift signal, power line interference signal, physiological interference signal, breathing signal, movement signal, myocardial signal, atrial signal, ventricular signal, or a set of extraneous signals. It will be appreciated that many extraneous signals may be advantageously removed or attenuated.

In one embodiment, the module 620 is constructed to remove the QRS signal, and detects R-waves in received signals, isolates individual QRS complex cycles based on the detected R-waves, calculates a reference cycle based on a plurality of the isolated cycles, and removes the reference cycle from the received ECG signals. The separation module 630 uses a non-orthogonal transformation method such as an ICA method to separate the intermediary signals into statistically substantially independent components. It will be understood that other separation processes may be used. The display module 640 displays one or more of the separated components on a screen, stores them in a computer or prints them on paper for medical analysis. The separated components can be used to detect medical conditions such as arrhythmia and atrial fibrillation.

The word "module" refers to one or more physical devices or computer instructions in hardware or software form that carry out certain functions. Modules can be combined or separated into fewer or more modules. Modules need not be located at the same physical location. For example, a module that records or receives ECG signals can be connected using a wired or wireless network to a remotely located module that removes QRS complex waves and separates the signals into independent components.

In one embodiment, the modules 610-640 of FIG. 6 can be integrated into one device. For example, an ECG device includes 3-lead sensors to record ECG signals from a patient, data storage unit to store the recorded ECG signals over a continuous time period, one or more processing units that process the stored signals to remove QRS complex signals and to separate the signals into independent components, and a display unit that displays the separated components. A physician or nurse can thus observe the separated components as ECG signals are recorded. In one embodiment, the receiving module 610 and the display module 640 are commercially available components. They are connected to the QRS complex removal module 620 and the separation module 630. The modules 620 and 630 include computer instructions in software or hardware form. For example, computer instructions for the modules 620 and 630 can be embodied in one or more microprocessor chips.

The above-described method was applied to actual patient data with good results, as shown in FIGS. 7A-7D. FIG. 7A illustrates a series of recorded 3-lead ECG signals over a continuous 10-second period. FIG. 7B illustrates the FIG. 7A signals with QRS complex signals substantially removed. The QRS complex signals are removed by producing a reference cycle based on detected R-waves and removing the reference cycle from the recorded signals. It will be appreciated that other specific methods may be used to remove the QRS signal.

FIG. 7C illustrates the FIG. 7B signals separated by an independent component analysis method into statistically independent components. In the example shown in FIG. 7C, the 1st component signals mainly represent the T wave signals following heartbeats, the 2nd component signals mainly represent not-removed QRS complex signal and a portion of T wave signals, and the 3rd component signals indicate a likely atrial fibrillation (AF) condition for the patient. In FIG. 7D, the 3rd component signals of FIG. 7C is back projected into the 1st lead signals of FIG. 7A, to compare a separated component with a recorded lead of signals.

In addition to atrial fibrillation, the disclosed system and method can also be utilized to detect other medical conditions. For example, a separated component that mainly represents T waves or ST segments (if ST segments exist), such as the 1st component in FIG. 7C, can be used to detect myocardial infarction. The separated components may be used to detect other conditions such as sinus arrhythmia, wandering atrial pacemaker, multifocal atrial tachycardia, atrial flutter, agonal rhythm, torsades de pointes, first-degree AV block, Wenchebach, type II second-degree AV block, and so forth. As described above, the separated components can be used to create a chaos phase space portrait.

Although the foregoing has described certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not to be limited by the preferred embodiments, but is to be defined by reference to the following claims.

What is claimed is:

1. A system for processing electrocardiogram (ECG) signals, the system comprising:
   a receiving module configured to receive a plurality of channels of ECG signals from a patient;
   a signal removal module configured to substantially remove an extraneous signal from the received ECG signals to produce intermediary signals;
   a separation module configured to separate the intermediary signals using a non-orthogonal transformation method to produce a plurality of statistically substantially independent components of signals;
   a display module configured to display one or more of the separated components of signals;
   a database storing a plurality of EKG signal triggers and one or more corresponding diagnoses; and
   a matching module configured to match the substantially independent components of signals with one or more of the stored EKG signal triggers, wherein at least one of the EKG signal triggers is based on history of the patient during an observation period.

2. The system of claim 1, wherein the receiving module is configured to receive 3-lead or 2-lead ECG signals.

3. The system according to claim 1 wherein the signal removal module is a filter constructed to substantially attenuate a QRS complex signal.

4. The system of claim 1, wherein the signal removal module is a QRS complex removal module that is configured to isolate signals for a plurality of QRS complex cycles within the received ECG signals.

5. The system of claim 4, wherein the QRS complex removal module is further configured to identify the plurality of QRS complex cycles by detecting an R-wave in each of the plurality of QRS complex cycles.

6. The system of claim 5, wherein the QRS complex removal module is configured to detect the R-wave by calculating correlation coefficients between at least a portion of the received ECG signals and a triangle template.

7. The system of claim 4, wherein the QRS complex removal module is configured to remove QRS reference cycle signals from the received ECG signals using a regression method.

8. The system of claim 4, wherein the QRS complex removal module is configured to remove QRS reference cycle signals from the received ECG signals using a match filter method.

9. The system of claim 1, wherein the separation module is configured to separate the intermediary signals using an independent component analysis method.

10. A computer-implemented method of separating electrocardiogram (ECG) recording signals, the method comprising:
    receiving a plurality of ECG channel signals of a patient;
    identifying an extraneous signal in the received ECG signals;
    substantially attenuating the extraneous signal in the received ECG signals to produce intermediary signals;
    separating the intermediary signals using a non-orthogonal transformation method to produce a plurality of statistically substantially independent components of signals; and
    storing a plurality of EKG signal triggers and one or more corresponding diagnoses; and algorithmically identifying a heart condition of the patient by matching the plurality of statistically substantially independent components of signals with one or more of the stored EKG signal triggers, wherein at least one of the EKG signal triggers is based on history of the patient during an observation period.

11. The method according to claim 10, wherein the step of substantially attenuating includes substantially removing a QRS signal.

12. The method according to claim 10, wherein the step of substantially attenuating includes removing a baseline drift signal, power line interference signal, physiological interference signal, breathing signal, movement signal, myocardial signal, atrial signal, and ventricular signal.

13. The method of claim 10, wherein the step of receiving a plurality of ECG channel signals comprises receiving 3 channels of ECG signals.

14. The method of claim 10, wherein the step of substantially attenuating includes substantially removing a QRS signal, the step of substantially removing comprises:
   identifying from the received ECG signals a plurality of signal cycles;
   isolating signals for the identified plurality of signal cycles;
   producing signals for a reference cycle based on the isolated signal cycles; and
   removing the reference cycle signals from the received ECG signals.

15. The method of claim 14, wherein the plurality of signal cycles comprises a plurality of QRS complex cycles.

16. The method of claim 14, wherein the plurality of signal cycles comprises a plurality of heartbeat cycles.

17. The method of claim 14, wherein the step of producing signals for a reference cycle comprises using a wavelet transformation method to produce signals for a reference cycle.

18. The method of claim 14, wherein the step of identifying the plurality of signal cycles comprises detecting an R-wave in each of the plurality of signal cycles.

19. The method of claim 18, further comprising calculating time intervals between adjacent detected R-waves, wherein the step of isolating signals for the identified plurality of signal cycles comprises isolating signals based on the detected R-waves and based on the calculated time intervals between adjacent detected R-waves.

20. The method of claim 10, wherein the step of separating the intermediary signals comprises separating the intermediary signals using an independent component analysis method.

21. The method of claim 10, wherein the separated components of signals are used by a physician to determine the likelihood of atrial fibrillation, arrhythmia, or myocardial infarction in the patient.

22. The method of claim 10, wherein the step of separating comprises:
   multiplying a vector of the intermediary signals by a scaling weights matrix to obtain scaled intermediary signals;
   adjusting the scaling matrix to reduce information redundancy among the scaled intermediary signals; and
   repeating the steps of multiplying and adjusting until the information redundancy among the scaled intermediary signals is reduced to a predetermined level.

23. The method of claim 10, wherein the step of separating comprises:
   multiplying a vector of the intermediary signals by a scaling weights matrix to obtain a matrix of first scaled intermediary signals;
   adding an initial weights matrix to the matrix of first scaled intermediary signals to obtain a second intermediary signals;
   adjusting the scaling matrix and the initial weights matrix to reduce information redundancy among the scaled intermediary signals; and
   repeating the steps of multiplying, adding, and adjusting until the information redundancy among the scaled intermediary signals is reduced to a predetermined level.

24. The method of claim 10, further comprising:
   using a neural network to compute a prediction weight; and
   computing from the intermediary signals and the prediction weight a linear mapping correlated with a physiological parameter of the patient.

* * * * *